(12) United States Patent
Parker et al.

(10) Patent No.: US 11,357,939 B2
(45) Date of Patent: Jun. 14, 2022

(54) BREATHING LUNG DEVICE

(71) Applicant: Gyrus ACMI, Inc., Westborough, MA (US)

(72) Inventors: Jay L. Parker, Redmond, WA (US); Gerald V. Rapp, San Diego, CA (US); Nathaniel S. Hague, Escondido, CA (US)

(73) Assignee: Gyrus Acmi, Inc., Westborough, MA (US)

( * ) Notice: Subject to any disclaimer, the term of this patent is extended or adjusted under 35 U.S.C. 154(b) by 952 days.

(21) Appl. No.: 16/101,043

(22) Filed: Aug. 10, 2018

(65) Prior Publication Data

US 2019/0351162 A1  Nov. 21, 2019

Related U.S. Application Data

(60) Provisional application No. 62/673,665, filed on May 18, 2018.

(51) Int. Cl.
 *A61M 16/00* (2006.01)
 *A61M 16/20* (2006.01)

(52) U.S. Cl.
 CPC .... *A61M 16/0057* (2013.01); *A61M 16/0009* (2014.02); *A61M 16/202* (2014.02); *A61M 16/207* (2014.02); *A61M 16/024* (2017.08); *A61M 2016/0027* (2013.01); *A61M 2205/3344* (2013.01); *A61M 2205/3355* (2013.01); *A61M 2210/1039* (2013.01)

(58) Field of Classification Search
 USPC .................................. 434/265; 435/284.1
 See application file for complete search history.

(56) References Cited

U.S. PATENT DOCUMENTS

| | | | | |
|---|---|---|---|---|
| 3,374,554 A * | 3/1968 | De Bella | ........... | G09B 23/28 434/272 |
| 4,167,070 A * | 9/1979 | Orden | ........... | G09B 23/32 434/272 |
| 4,437,461 A * | 3/1984 | Greenberg | ........... | A61M 16/20 128/205.24 |
| 6,581,596 B1 * | 6/2003 | Truitt | ........... | A61M 16/0051 128/204.21 |
| 7,770,578 B2 * | 8/2010 | Estes | ........... | A61M 16/0069 128/204.18 |
| 2004/0221852 A1 * | 11/2004 | Madsen | ........... | A61M 16/0463 128/207.14 |
| 2004/0231670 A1 * | 11/2004 | Bassin | ........... | A61M 16/20 128/204.18 |
| 2011/0065169 A1 * | 3/2011 | Steen | ........... | A01N 1/0242 435/284.1 |
| 2013/0008444 A1 * | 1/2013 | Chalvignac | ........... | A61M 16/0051 128/204.21 |

(Continued)

*Primary Examiner* — Colin W Stuart
(74) *Attorney, Agent, or Firm* — Schwegman Lundberg & Woessner, P.A.

(57) ABSTRACT

A device for placing a lung in a variety of different inflation states using positive air pressure. An exemplary device includes a housing and an air supply component. The housing includes a platform receives at least one of a synthetic lung or a real lung. The platform is at the same air pressure as a surrounding environment. The air supply component is located within the one or more internal cavities of the housing. The air supply component inflates the synthetic lung or the real lung with positive pressure.

16 Claims, 8 Drawing Sheets

(56) References Cited

U.S. PATENT DOCUMENTS

| | | | |
|---|---|---|---|
| 2014/0290659 A1* | 10/2014 | Chen | A61M 16/202 |
| | | | 128/205.24 |
| 2015/0027443 A1* | 1/2015 | Barr | A61M 16/0808 |
| | | | 128/203.12 |
| 2016/0310694 A1* | 10/2016 | Arnott | A61M 16/0875 |
| 2020/0164166 A1* | 5/2020 | Darwood | A61M 16/00 |
| 2020/0349863 A1* | 11/2020 | Jensen | G09B 23/288 |

* cited by examiner

BREATHING LUNG DEVICE

PRIORITY CLAIM

This application claims the benefit of U.S. Provisional Patent Application Ser. No. 62/673,665, filed 18 May 2018, the contents of which are hereby incorporated by reference.

BACKGROUND

Simulation devices for ventilating ex vivo lungs, e.g., plasticized or animal, typically use negative pressure to inflate the lungs. For example, lungs may be ventilated utilizing a negative pressure (i.e., below atmospheric pressure) around the lungs to allow the lungs to naturally fill with ventilation gas that is at or near atmospheric pressure. This technique requires the lungs to be maintained in a sealed chamber. These devices are difficult to operate without training and fail to provide a meaningful training/user experience. Alternative techniques use high pressure reservoirs (~50 psi) to operate valves requiring the use of compressed oxygen or air from tanks or compressors adding complexity, size, and noise to the system.

SUMMARY

The present invention includes a device for presenting a breathing lung using positive low-pressure air. An exemplary device includes a housing and an air supply component. The housing includes a platform that receives at least one of a synthetic lung or a real lung. The platform is at the same pressure as a surrounding environment. The air supply component is located within the one or more internal cavities of the housing. The air supply component inflates the synthetic lung or the real lung with positive low-pressure air.

In one aspect of the invention, the air supply component includes a pneumatic diaphragm pump, a valve, and a controller. Other types of pumps can also be used, such as vane, scroll, and piston. The valve includes a first port pneumatically coupled to the pneumatic pump, a second port configured to be in pneumatic communication with the synthetic lung or the real lung, and a third port for venting. The controller causes the valve to alternate between connecting the first port to the second port and the second port to the third port.

In another aspect of the invention, the air supply component includes a pressure sensor configured to generate a pressure value and send the pressure value to the controller. The pressure sensor is located between the second port and the synthetic lung or the real lung. The controller instructs the valve to connect the first port to the second port, if the pressure value drops below a first threshold value. The controller instructs the valve to connect the second port to the third port, if the pressure value goes above a second threshold value.

In still another aspect of the invention, the air supply component includes a first user control configured to allow a user to change the value of the first threshold value.

In yet further aspects of the invention, the air supply component includes a second user control configured to allow a user to change the value of the second threshold value.

In other aspects of the invention, the air supply component includes a pump speed control configured to allow a user to change a speed of a motor of the pneumatic pump to enable variable inspiration rates.

In yet other aspects of the invention, the air supply component includes a fitting having a first opening configured to be coupled to the synthetic lung or the real lung, a second opening coupled to the second port of the valve, and a third opening. The synthetic lung or the real lung is connected to the first opening. The fitting allows a medical device to pass into the synthetic lung or the real lung via the third and first openings.

In still yet other aspects of the invention, the air supply component includes an air lock device coupled to the third opening. The air lock device may be custom made or may be an off-the-shelf device.

Further features, advantages, and areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 9-1 shows a perspective view of the device of FIG. 5; and

FIG. 9-2 shows a partial view of the device of FIG. 9-1.

DETAILED DESCRIPTION

The following description is merely illustrative in nature and is not intended to limit the present disclosure, application, or uses. The following description explains, by way of illustration only and not of limitation, various embodiments of devices for providing an interactive breathing lung device as well as methods of operating and of using the same. It will be appreciated that various embodiments described herein may help to simplify the process of tissue aspiration.

Figure 1:
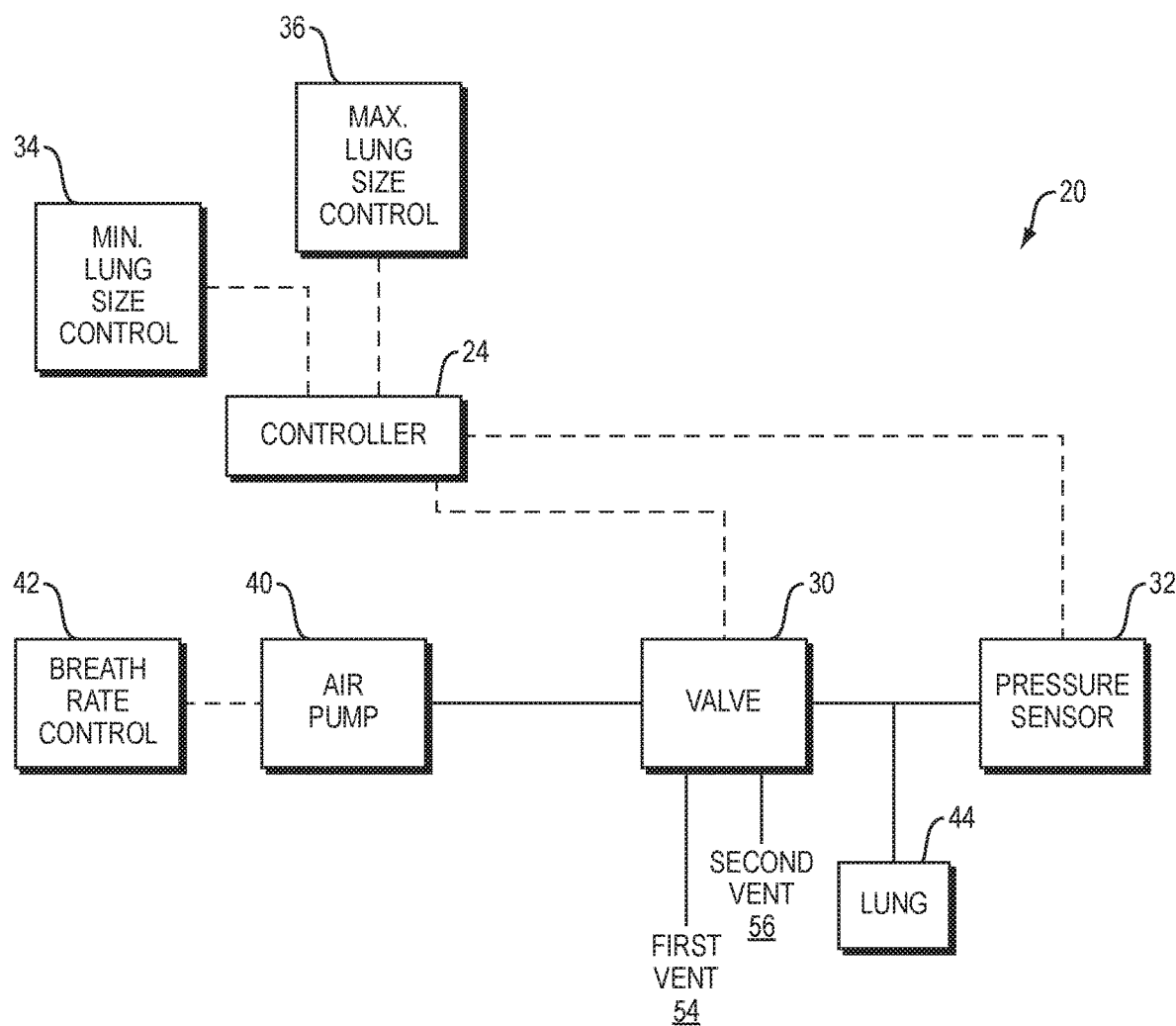
FIG. 1 shows a block diagram of a system formed in accordance with an embodiment of the present invention.

FIG. 1 shows an interactive lung breathing system 20 for demonstration and interactive training purposes. The system 20 includes numerous components that are linked either via pneumatic connections (i.e., solid lines between blocks) and/or wired or wireless signal communication connections (i.e., dashed lines between blocks). The system 20 includes a controller 24 that is in signal communication with a valve 30, a pressure sensor 32, a minimum lung size control device 34 and a maximum lung size control device 36. The system 20 also includes an air pump 40 that is in wired or wireless signal communication with a breath rate control device 42. The air pump 40 is in pneumatic communication/connection with the valve 30. The valve 30 is in pneumatic communication with the pressure sensor 32 and a lung 44 (e.g., animal or synthetic lungs). The pressure sensor 32 samples at a predefined sampling rate that allows for smooth transitions between inspiration and expiration modes.

The controller 24 provides a valve control signal to the valve 30 based on a minimum lung size value provided by the minimum lung size control device 34, a maximum lung size value provided by the maximum lung size control device 36 and an air pressure value provided by the pressure sensor 32. The controller 24 may include a programmable logic controller, a hardwired/solid-state controller or a comparable signal processing/controlling device, such as a microprocessor with associated circuitry. The controls 34, 36, 42 may include potentiometers or comparable devices.

The air pump 40 receives a breath rate signal from the breath rate control device 42. This controls the amount of airflow generated by the air pump 40. The speed of the motor of the air pump 40 is based on the value of the breath rate signal. The air pump 40 supplies air to the valve 30. In one embodiment, the valve 30 is a four-way valve that includes a spring return solenoid controlled by the valve control signal produced by the controller 24. An exemplary valve is produced by Humphrey Products Corporation. The valve control signal causes the valve 30 to either allow air received from the air pump 40 to pass into the lung 44 or cause the air from the air pump 40 to be diverted to a first vent port 54 and connect the lung 44 to a second vent port 56. In one embodiment, the first vent port 54 or additional tubing attached to the first vent port 54 is positioned in order to direct air to the air pump 40 in order to provide a cooling effect to a motor of the air pump 40. The atmospheric pressure adjacent to the first and second vent ports 54, 56 is at standard atmospheric pressure. An exemplary air pump 40 is a high flow diaphragm pump, such as that produced by Parker-Hannifin Corporation.

Figure 2:
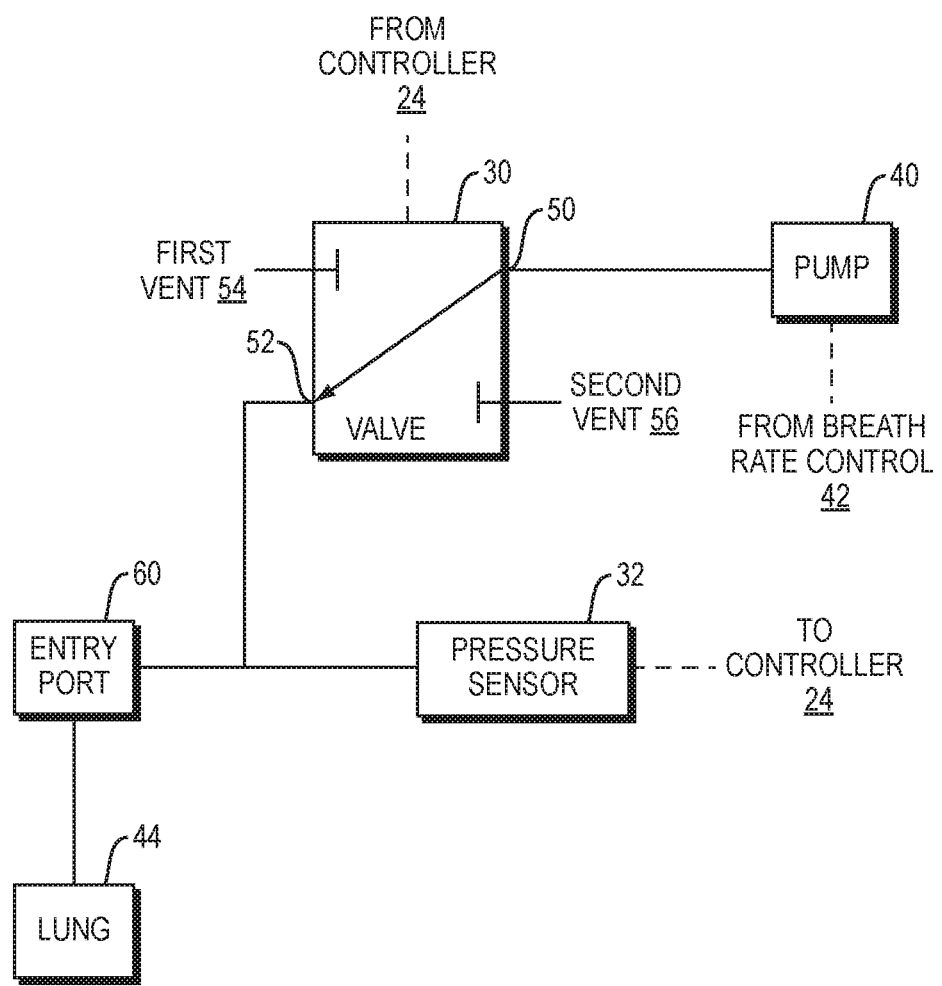
FIG. 2 shows a diagram of components of the system of FIG. 1 in a first operational state.

FIG. 2 shows a first pneumatic mode of operation of the system 20. The first pneumatic mode of operation is a lung inspiration or inhale mode. In the first pneumatic mode of operation, the valve 30 is commanded by the valve control signal received from the controller 24 to direct air received from the air pump 40 at a pump port 50 to a lung port 52 that connects to the lung 44. The pressure sensor 32 is connected between the lung 44 and the lung port 52. In the first pneumatic mode of operation, the lung 44 inflates at a rate determined by the breath control signal received from the breath rate control device 42. Thus, the lung 44 inflates using positive air pressure. The first pneumatic mode of operation is initiated either upon start-up of the system 20 or whenever the pressure value, sensed by the pressure sensor 32, drops below the minimum lung size value provided by the minimum lung size control device 34. The minimum lung size value equates to a pressure value.

Figure 3:
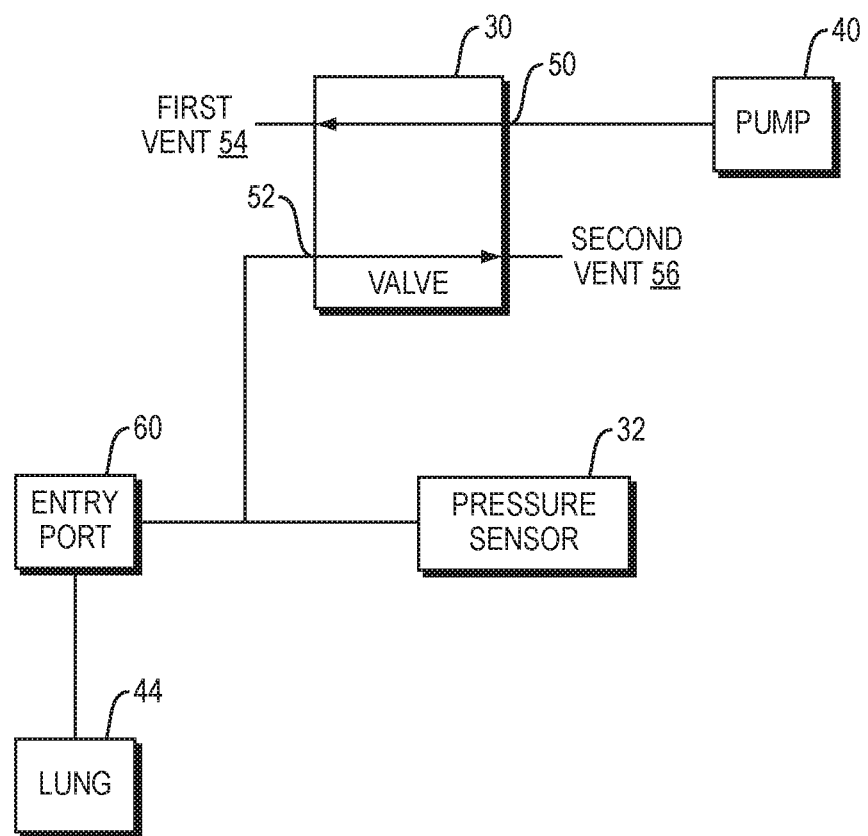
FIG. 3 shows a diagram of components of the system of FIG. 1 in a second operational state.

FIG. 3 shows a second pneumatic mode of operation of the system 20. The second pneumatic mode of operation is a lung deflate or expiration mode. In the second pneumatic mode of operation, the valve 30 is commanded by the valve control signal received from the controller 24 to direct air received from the pump 40 to be vented out of the first vent port 54. Also, the valve 30 is commanded by the valve control signal to connect the lung port 52 to the second vent port 56. The inflated lung 44 starts deflating due to this pneumatic connection to lower pressure (i.e., standard atmospheric pressure) at the second vent port 56.

The second pneumatic mode of operation is initiated when the pressure value sensed by the pressure sensor 32 goes above the maximum lung size value provided by the maximum lung size control device 36. The maximum lung size value equates to a pressure value.

The system 20 may include a pressure relief valve (not shown) located between the valve 30 and the lung 44. The pressure relief valve would be set to relieve air pressure in the lung 44 in the case where the valve 30 remained in the inspiration mode.

As shown in FIGS. 2 and 3, a sealable entry or access port 60 is provided between the lung 44 and the lung port 52. The sealable access port 60 allows one to insert medical devices (e.g., scopes, cameras, tools) into the lung 44 as the system 20 transitions between the inspiration and expiration states. The sealable access port 60 provides a seal or a minimal leakage seal around the medical device inserted into the lung 44. The sealable access port 60 allows user to test and/or interactively train on equipment designed for use in a lung. For example, one can insert various types of scopes or tools, such as a lung valve (e.g., IBV® produced by Spiration, Inc.), imaging devices, delivery catheters, tissue sampling or treatment devices, etc.

Figure 4:
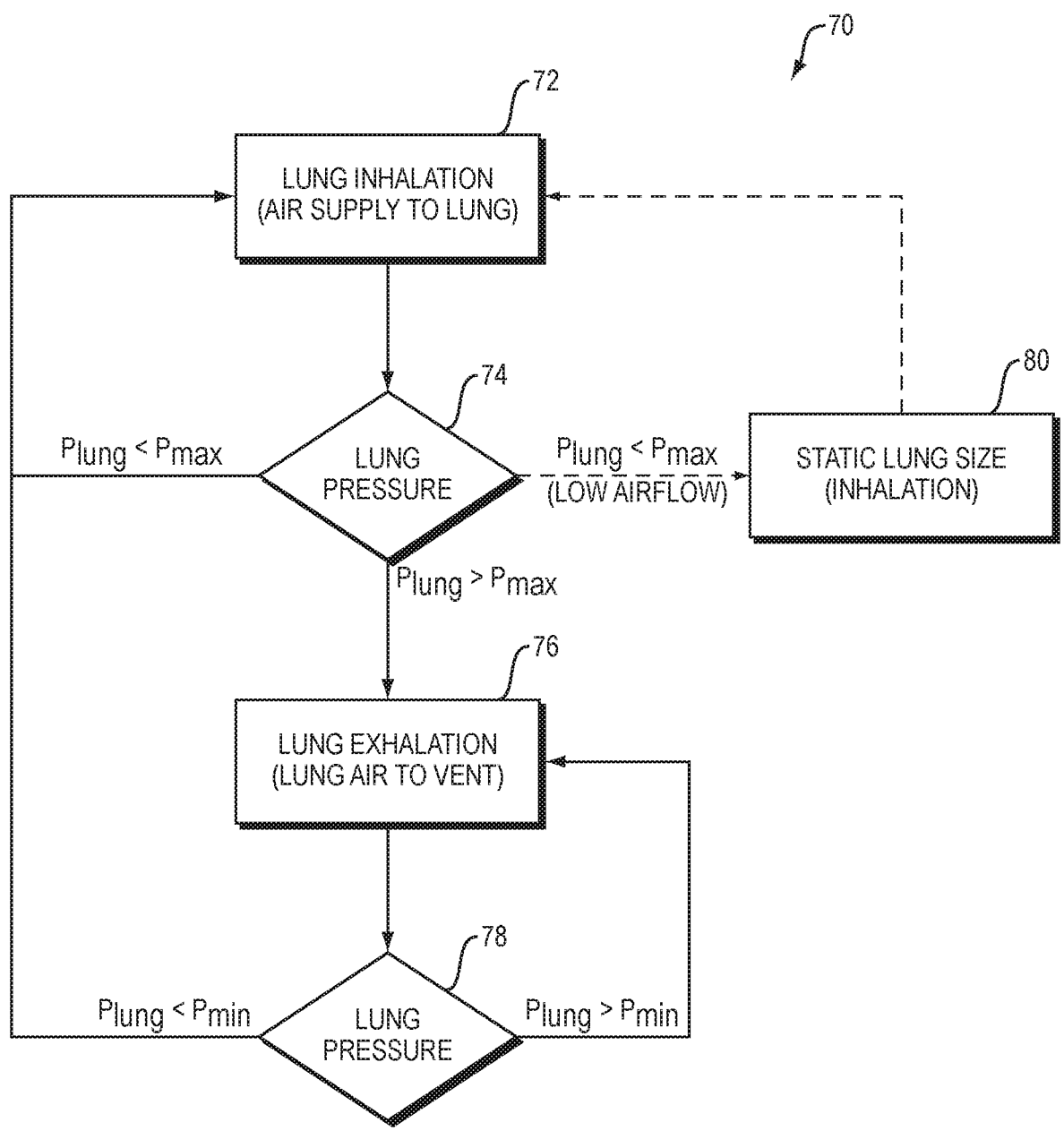
FIG. 4 shows a diagram of a process performed by the system shown in FIG. 1.

FIG. 4 shows an exemplary flow diagram of a process 70 performed by the system 20 shown in FIG. 1. First, at a step 72, the system 20 is activated and air is supplied to an attached lung by the air pump 40, thus inflating the lung—simulating taking a breath. The air pump 40 supplies air at a previously selected speed (i.e., the breath rate control device 42) or a default speed (i.e., air pump motor speed (volume of air/second)). Next, at a decision step 74, the controller 24 provides commands to the valve 30 based on an air pressure value (Ptung) received from the pressure sensor 32. If Ptung is less than a predefined maximum air pressure threshold value (Pmax) (set by the maximum lung size control device 36), the process 70 returns to step 72. If Ptung is greater than Pmax, the process 70 continues to step 76. At step 76, the valve 30 is commanded by the controller 24 to vent lung air, thus causing the lung to deflate—simulating breathing out.

Next, at a decision block 78, if Ptung is greater than a predefined minimum air pressure threshold value (Pmin) (set by the minimum lung size control device 34), the process 70 remains in the lung exhalation mode of step 76. If Ptung is less than Pmin, the process 70 returns to lung inhalation of step 72.

In one embodiment, in a low airflow mode of operation, as shown at step 80, the max lung control device 36 is set to a maximum (or higher than will be tripped) and the breath rate control device 42 is set low enough whereby the air pump rate is matched to a set leak rate (hole in the air system-lung side) causing the lung to remain inflated at a particular size depending on the breath rate control (air pump output). The air pressure never reaches the trip point and so the lung stays inflated at a particular size. This allows the lung to be kept at variable inflated states indefinitely.

Figure 5:
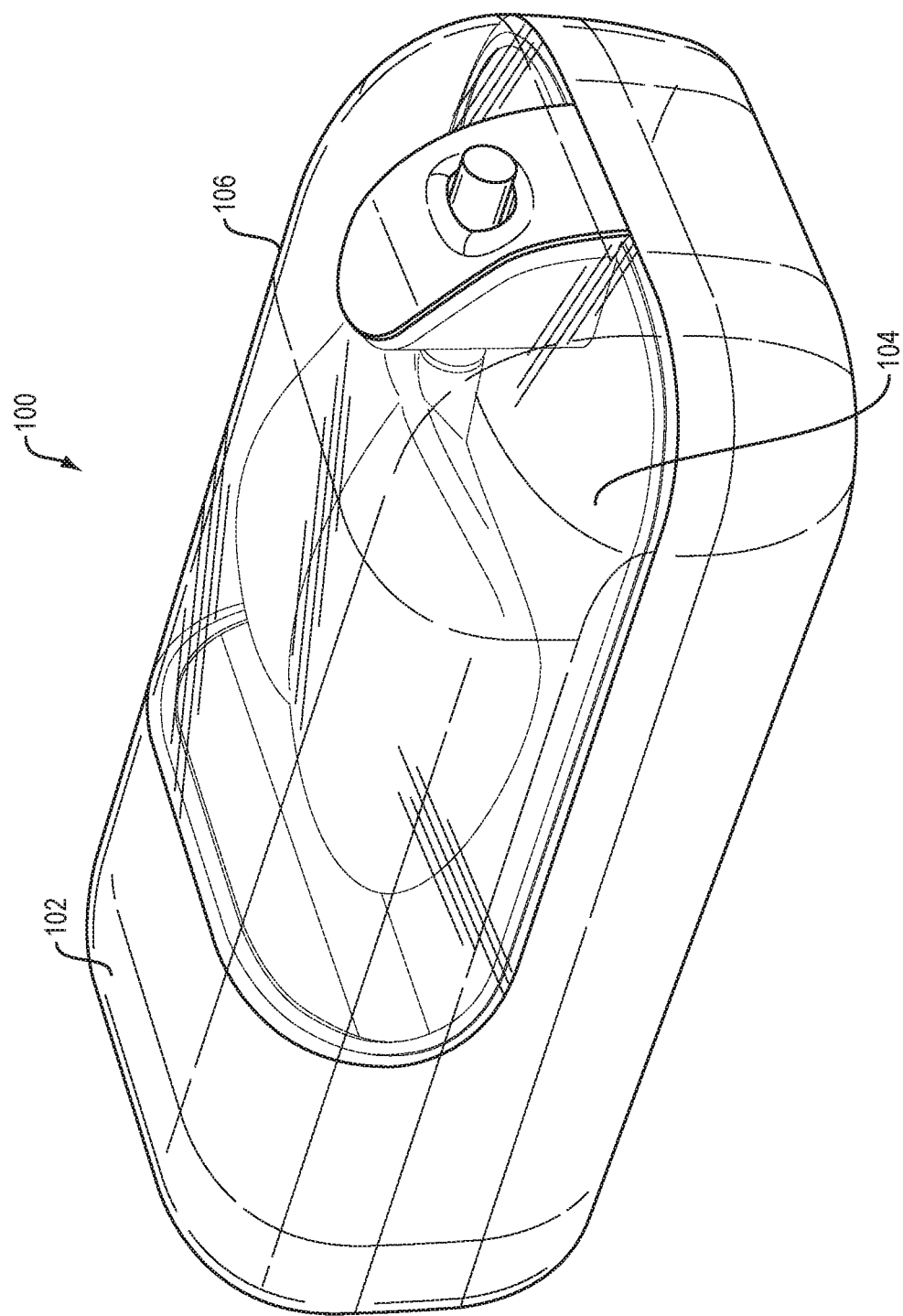
FIG. 5 shows a perspective view of an exemplary device configured to house the system of FIG. 1.
Figure 6:
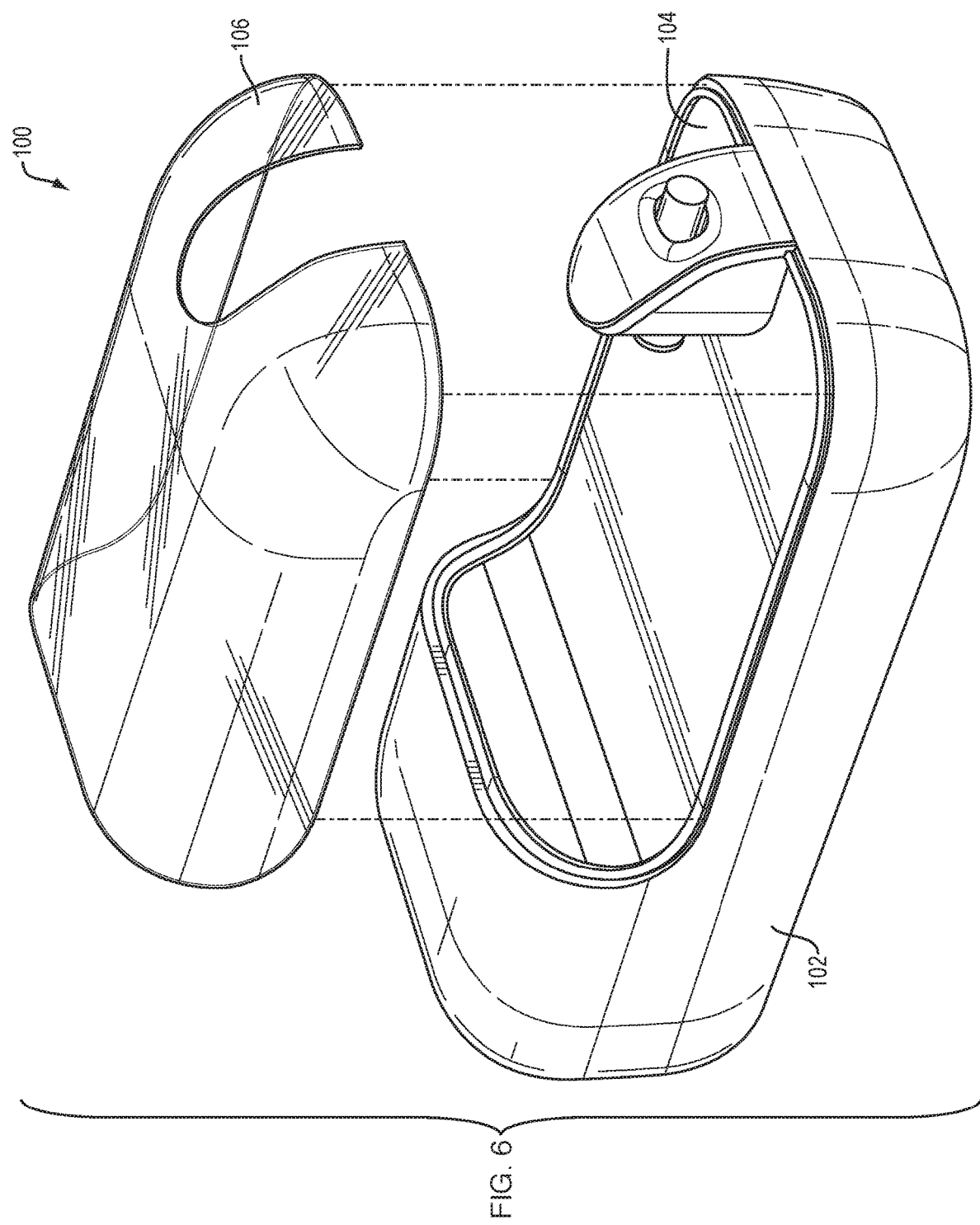
FIG. 6 shows a perspective view of the device of FIG. 5.
Figure 7:
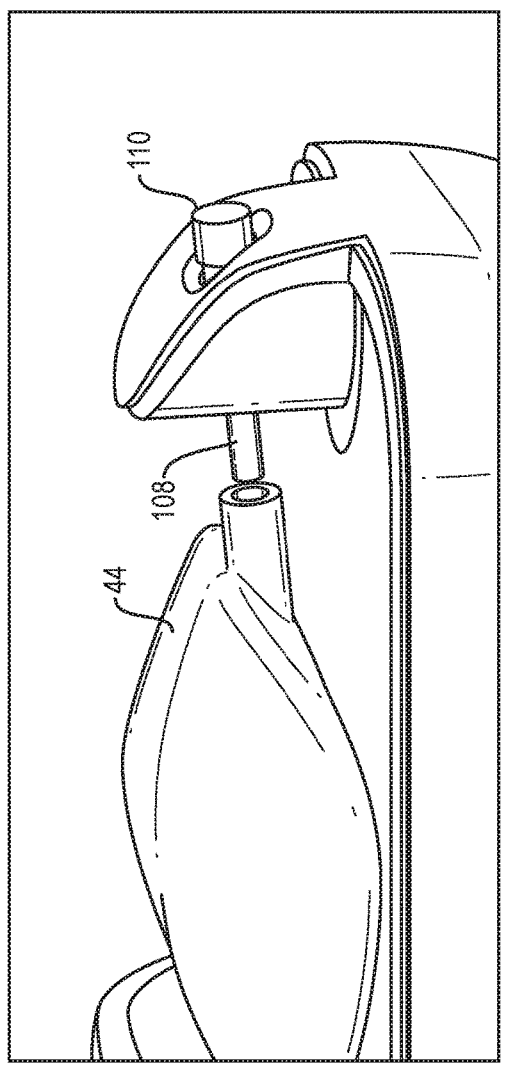
FIG. 7 shows a partial perspective view of the device of FIG. 5.
Figure 8:
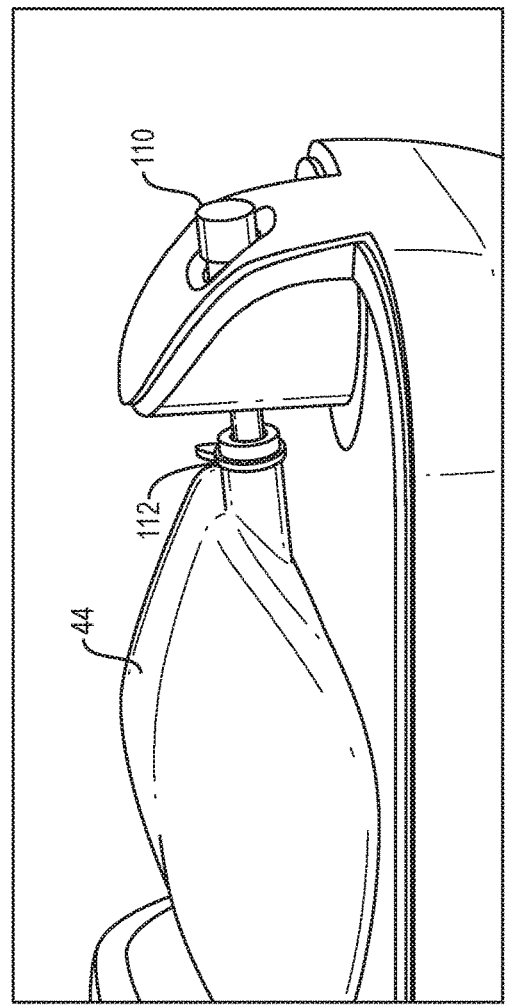
FIG. 8 shows a partial perspective view of the device of FIG. 5.

FIGS. 5 and 6 are perspective views of a lung box 100 configured to house the components of the system 20 of FIG. 1. The lung box 100 includes a housing 102 and a transparent cover 106. The housing 102 includes a platform 104 that supports a lung. The transparent cover 106 covers the platform 104 to allow for viewing of the received lung. The transparent cover 106 rests on receiving edges of the housing 102. In order to operate, the transparent cover 106 is removed, then the lung 44 is placed on the platform 104—FIG. 7. Next, the lung 44 is connected to a fitting 108 (e.g., a barbed fitting) and secured with a clamp device 112 to prevent leaks—FIG. 8. The transparent cover 106 is replaced but does not need to be replaced for the system 20 to function.

Figures 2, 9:
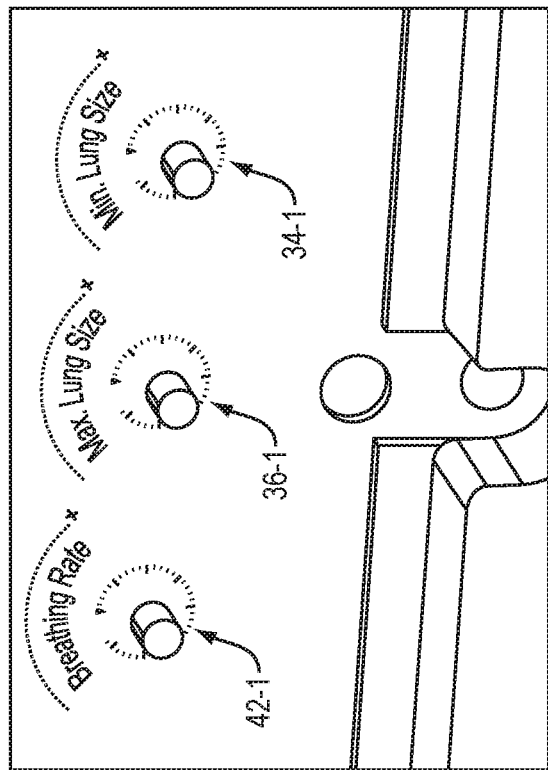
Figures 1, 9:
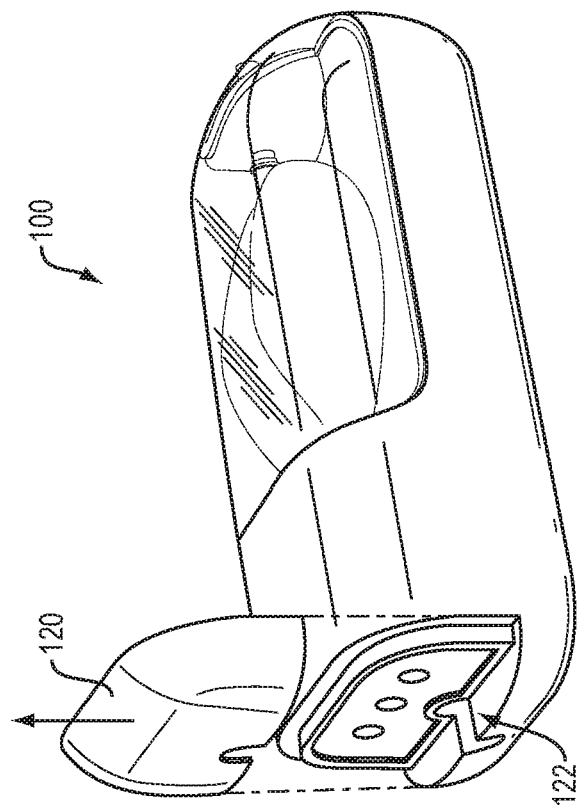

FIG. 9-1 shows a perspective view of the lung box 100 with a controls cover 120 removed to reveal a multiple controls area 122. FIG. 9-2 is a front view of the multiple controls area 122. The multiple controls area 122 includes a breathing rate control knob 42-1, a maximum lung size control knob 36-1, and a minimum lung size control knob 34-1. The control knobs 42-1, 36-1, 34-1 are connected to previously calibrated potentiometers (not shown) or other devices capable of producing a plurality of different signals.

In one embodiment, the controller 24 is configured to manage the extra air leakage around an entry port 110. The entry port 110 receives the sealable access port 60. However, some air may leak out the sealable access port 60 due to various reasons. The controller 24 can alter the breathing rate in order to compensate for a predefined amount of leakage.

EMBODIMENTS

A. A system comprising: a pneumatic pump; a valve comprising: a first port pneumatically coupled to the pneumatic pump; a second port configured to be in pneumatic communication with at least one of a synthetic lung or a real lung; and a third port for venting; and a controller configured to cause the valve to alternate between connecting the first port to the second port and the second port to the third port.

B. The system of A, further comprising a pressure sensor configured to generate a pressure value and send the pressure value to the controller, the pressure sensor being located between the second port and the synthetic lung or the real lung, wherein the controller instructs the valve to connect the first port to the second port, if the pressure value drops below a first threshold value, wherein the controller instructs the valve to connect the second port to the third port, if the pressure value goes above a second threshold value.

C. The system of B, wherein the valve further comprises a fourth port for venting, wherein the controller further instructs the valve to connect the first port to the fourth port, if the pressure value goes above the second threshold value.

D. The system of B, further comprising a first user control device configured to allow a user to change the value of the first threshold value.

E. The system of D, wherein the first user control device comprises at least one of a potentiometer or a digital switch.

F. The system of B, C, D or E, further comprising a second user control device configured to allow a user to change the value of the second threshold value.

G. The system of F, wherein the second user control device comprises at least one of a potentiometer or a digital switch.

H. The system of any of A-G, further comprising a pump speed control device configured to allow a user to change an amount of airflow produced by the pneumatic pump.

I. The system of H, wherein the pump speed control device comprises at least one of a potentiometer or a digital switch.

J. The system of any of A-I, further comprising a fitting comprising: a first opening configured to be coupled to the synthetic lung or the real lung; a second opening coupled to the second port of the valve; and a third opening, wherein when the synthetic lung or the real lung is connected to the first opening, the fitting is configured to allow a medical device to pass into the synthetic lung or the real lung via the first and third openings.

K. The system of J, further comprising an air lock device coupled to the third opening.

L. A device comprising: a housing comprising: a platform configured to receive at least one of a synthetic lung or a real lung, the platform being at the same pressure as a surrounding environment; and one or more internal cavities; and an air supply component located within the one or more internal cavities of the housing, the air supply component configured to inflate the synthetic lung or a real lung with positive pressure.

M. The device of L, wherein the air supply component comprises: a pneumatic pump; a valve comprising: a first port pneumatically coupled to the pneumatic pump; a second port configured to be in pneumatic communication with the synthetic lung or the real lung; and a third port for venting; and a controller configured to cause the valve to alternate between connecting the first port to the second port and the second port to the third port.

N. The device of M, wherein the air supply component further comprises a pressure sensor configured to generate a pressure value and send the pressure value to the controller, the pressure sensor being located between the second port and the synthetic lung or the real lung, wherein the controller instructs the valve to connect the first port to the second port, if the pressure value drops below a first threshold value, wherein the controller instructs the valve to connect the second port to the third port, if the pressure value goes above a second threshold value.

O. The device of N, wherein the air supply component further comprises a first user control device configured to allow a user to change the value of the first threshold value.

P. The device of N or O, wherein the air supply component further comprises a second user control device configured to allow a user to change the value of the second threshold value.

Q. The device of any of L-P, wherein the air supply component further comprises a pump speed control device configured to allow a user to change amount of airflow by changing speed of a motor of the pneumatic pump.

R. The device of any of L-Q, wherein the air supply component further comprises a fitting comprising: a first opening configured to be coupled to the synthetic lung or the real lung; a second opening coupled to the second port of the valve; and a third opening, wherein when the synthetic lung or the real lung is connected to the first opening, the fitting is configured to allow a medical device to pass into the synthetic lung or the real lung via the first and third openings.

S. The device of R, wherein the air supply component further comprises an air lock device coupled to the third opening.

T. The device of M, wherein the valve further comprises a fourth port for venting air towards the pneumatic pump, wherein the controller further instructs the valve to connect the first port to the fourth port, if the pressure value goes above the second threshold value.

The description of the invention is merely exemplary in nature and variations that do not depart from the gist of the invention are intended to be within the scope of the invention. Such variations are not to be regarded as a departure from the spirit and scope of the invention.

Although the preferable embodiments of the present invention have been described hitherto, the present invention is not limited to these embodiments. Additions, omissions, substitutions, and other modifications can be made without departing from the spirit or scope of the present invention.

In addition, the invention is not limited by the above description and is limited by only the scope of appended claims.

What is claimed is:

1. A system comprising:
 a pneumatic pump;
 a valve comprising:
  a first port pneumatically coupled to the pneumatic pump;
  a second port configured to be in pneumatic communication with an ex vivo lung; and
  a third port for venting;
 a controller configured to cause the valve to alternate between connecting the first port to the second port and the second port to the third port, thereby allowing air from the pneumatic pump to cause the ex vivo lung to simulate breathing;
 a sealable access port configured to be located between the second port and the ex vivo lung, wherein the sealable access port is configured to allow a medical device to pass therethrough;
 a minimum lung size control device configured to allow a user to set a minimum air pressure threshold value for the controller;
 a maximum lung size control device configured to allow a user to set a maximum air pressure threshold value selected to inflate the ex vivo lung, thus causing the ex vivo lung to simulate breathing in up to the maximum air pressure threshold value; and and
 a breath rate control device configured to allow a user to control speed for the pneumatic pump.

2. The system of claim 1, further comprising a pressure sensor configured to generate a pressure value and send the pressure value to the controller, the pressure sensor configured to be located between the second port and the ex vivo lung,
 wherein the controller instructs the valve to connect the first port to the second port, if the pressure value drops below the minimum air pressure threshold value,
 wherein the controller instructs the valve to connect the second port to the third port, if the pressure value goes above the maximum air pressure threshold value.

3. The system of claim 1, further comprising a pressure sensor configured to generate a pressure value and send the pressure value to the controller,
 wherein the valve further comprises a fourth port for venting,
 wherein the controller further instructs the valve to connect the first port to the fourth port, if the pressure value goes above the maximum air pressure threshold value.

4. The system of claim 1, wherein the minimum lung size control device comprises at least one of a potentiometer or a digital switch.

5. The system of claim 1, wherein the maximum lung size control device comprises at least one of a potentiometer or a digital switch.

6. The system of claim 1, wherein the breath rate control device comprises at least one of a potentiometer or a digital switch.

7. The system of claim 1, further comprising a fitting comprising:
 a first opening configured to be coupled to the ex vivo lung;
 a second opening coupled to the second port of the valve; and
 a third opening,
 wherein when the ex vivo lung is connected to the first opening, the fitting is configured to allow a medical device to pass into the ex vivo lung via the first and third openings.

8. The system of claim 7, further comprising an air lock device coupled to the third opening.

9. A device comprising:
 a housing comprising:
  a platform configured to receive an ex vivo lung, the platform being at the same pressure as a surrounding environment; and
  one or more internal cavities; and
 an air supply component located within the one or more internal cavities of the housing, the air supply component configured to inflate the ex vivo lung with positive pressure, thereby causing the ex vivo lung to simulating breathing;
 a minimum lung size control device configured to allow a user to set a minimum air pressure threshold value for the air supply component;
 a maximum lung size control device configured to allow a user to set a maximum air pressure threshold value for the air supply component selected to inflate the ex vivo lung, thus causing the ex vivo lung to simulate breathing in up to the maximum air pressure threshold value; and
 a breath rate control device configured to allow a user to control speed for the air supply component.

10. The device of claim 9, wherein the air supply component comprises:
 a pneumatic pump;
 a valve comprising:
  a first port pneumatically coupled to the pneumatic pump;
  a second port configured to be in pneumatic communication with the ex vivo lung; and
  a third port for venting; and
 a controller configured to cause the valve to alternate between connecting the first port to the second port and the second port to the third port.

11. The device of claim 10, wherein the air supply component further comprises a pressure sensor configured to generate a pressure value and send the pressure value to the controller, the pressure sensor configured to be located between the second port and the ex vivo lung,
 wherein the controller instructs the valve to connect the first port to the second port, if the pressure value drops below a first threshold value,
 wherein the controller instructs the valve to connect the second port to the third port, if the pressure value goes above a second threshold value.

12. The device of claim 11, wherein the air supply component further comprises a fitting comprising:
 a first opening configured to be coupled to the ex vivo lung;
 a second opening coupled to the second port of the valve; and
 a third opening,
 wherein when the ex vivo lung is connected to the first opening, the fitting is configured to allow a medical device to pass into the ex vivo lung via the first and third openings.

13. The device of claim 12, wherein the air supply component further comprises an air lock device coupled to the third opening.

14. The device of claim 11, wherein the valve further comprises a fourth port for venting air towards the pneumatic pump,
    wherein the controller further instructs the valve to connect the first port to the fourth port, if the pressure value goes above the second threshold value.

15. The device of claim 9, further comprising:
a sealable access port configured to be located adjacent the platform between the air supply component and the ex vivo lung, wherein the sealable access port is configured to allow a medical device to pass therethrough.

16. A device comprising:
a housing comprising:
    a platform configured to receive an ex vivo lung, the platform being at the same pressure as a surrounding environment; and
    one or more internal cavities;
an air supply component located within the one or more internal cavities of the housing, the air supply component configured to inflate the ex vivo lung with positive pressure; and
a sealable access port configured to be located between the air supply component and the ex vivo lung, wherein the sealable access port is configured to allow a medical device to pass therethrough.

\* \* \* \* \*